(12) United States Patent
Wang et al.

(10) Patent No.: US 11,708,386 B2
(45) Date of Patent: Jul. 25, 2023

(54) ULTRASONIC-MICROWAVE SYNERGISTIC EXTRACTION METHOD OF TOTAL SAPONINS IN BEAUTIFUL MILLETTIA ROOT

(71) Applicant: Tropical Crops Genetic Resources Institute, Chinese Academy of Tropical Agricultural Sciences, Haikou (CN)

(72) Inventors: Maoyuan Wang, Haikou (CN); Qing Yang, Haikou (CN); Qinglong Wang, Haikou (CN); Zhunian Wang, Haikou (CN); Xiaoxia Yan, Haikou (CN); Huan Tang, Haikou (CN); Yingying Li, Haikou (CN)

(73) Assignee: TROPICAL CROPS GENETIC RESOURCES INSTITUTE, CHINESE ACADEMY OF TROPICAL AGRICULTURAL SCIENCES, Hainan (CN)

( * ) Notice: Subject to any disclaimer, the term of this patent is extended or adjusted under 35 U.S.C. 154(b) by 0 days.

(21) Appl. No.: 17/946,531

(22) Filed: Sep. 16, 2022

(65) Prior Publication Data
US 2023/0088357 A1    Mar. 23, 2023

(30) Foreign Application Priority Data
Sep. 18, 2021    (CN) .......................... 202111112738.3

(51) Int. Cl.
*C07H 1/08*    (2006.01)
*B01D 11/02*    (2006.01)
*B01D 11/04*    (2006.01)

(52) U.S. Cl.
CPC ............ *C07H 1/08* (2013.01); *B01D 11/0211* (2013.01); *B01D 11/0265* (2013.01); *B01D 11/0288* (2013.01); *B01D 11/0419* (2013.01); *B01D 11/0423* (2013.01)

(58) Field of Classification Search
None
See application file for complete search history.

(56) References Cited

FOREIGN PATENT DOCUMENTS

| CN | 102793741 A | 11/2012 |
| CN | 104107208 A | 10/2014 |
| CN | 110025645 A | 7/2019 |
| CN | 113171390 A | 7/2021 |

OTHER PUBLICATIONS

Wang et al., "Metabolomic profiling of M. speciosa champ at different growth stages" Food Chemistry vol. 376 pp. 1-13 https://doi.org/10.1016/j.foodchem.2021.131941 (Year: 2021).*
Chan et al., "Microwave-assisted extractions of active ingredients from plants" Journal of Chromatography A vol. 1218 pp. 6213-6225 doi:10.1016/j.chroma.2011.07.040 (Year: 2011).*
CN Decision to Grant Patent Right, issued by China National Intellectual Property Administration, dated Feb. 23, 2022, 5 pages.

* cited by examiner

*Primary Examiner* — Eric Olson
(74) *Attorney, Agent, or Firm* — Muncy, Geissler, Olds & Lowe, P.C.

(57) ABSTRACT

The present disclosure provides an ultrasonic-microwave synergistic extraction method of total saponins in beautiful *millettia* root, comprising the following steps: S1, material treatment, S2, cold soaking, S3 enzymatic hydrolysis, S4 extract extraction, and S5 ultrasonic-microwave synergistic extraction. The extraction method of the present disclosure extracts relatively high content of total saponins, and has relatively high yield of saponins and low content of impurities, and each step acts synergistically to solve the problems of relatively low total saponin content, more impumayrities and bubbling in the extraction process.

1 Claim, No Drawings

ULTRASONIC-MICROWAVE SYNERGISTIC EXTRACTION METHOD OF TOTAL SAPONINS IN BEAUTIFUL MILLETTIA ROOT

FIELD OF TECHNOLOGY

The present disclosure relates to the technical field of plant extraction and in particular to an ultrasonic-microwave synergistic extraction method of total saponins in beautiful *millettia* root.

BACKGROUND

Beautiful *millettia* root is also named as *radix millettiae* speciosae. Beautiful *millettia* root is a dry root of *Millettia specisoa* belonging to *Millettia, Leguminosae*, has a sweet taste and a mild nature, and has effects on supplementing deficiency and moistening the lungs, and strengthening tendons and activating meridians and collaterals. In recent years, researches on chemical components of beautiful *millettia* root show that beautiful *millettia* root mainly contains active ingredients of flavonoids, carbohydrates, saponins, and alkaloid compounds, has functions of protecting the liver, enhancing immunity, preventing fatigue, expectorating phlegm, relieving cough, etc., and is a plant resource with a certain health-care effect and worthy of in-depth research and extensive promotion. The existing extraction methods of total saponins in beautiful *millettia* root mostly all aim at saponin components in alcohol-soluble components, wherein the content of extracted total saponins is 50-80%. Even if the high-content total saponins are obtained, column chromatography is required to be performed for many times. The method directly separates and purifies an extracting solution containing a large amount of impurities through a macroporous adsorption resin column, resulting a large loss of effective components while impurities are removed, a high cost, and an incomplete removal of impurities. Patent CN102793741A discloses a beautiful *millettia* root full-component extract and a preparation method and use thereof, and provides an alcohol extraction method of a beautiful *millettia* root component, but an effect on an extraction process of saponins is poor. Patent CN110025645B discloses a method for extracting total saponins of American *ginseng*. However, the purity of the extracted saponins is still relatively low through column chromatography for multiple times.

SUMMARY

In view of this, the present disclosure provides an ultrasonic-microwave synergistic extraction method of total saponins in beautiful *millettia* root.

The technical solution of the present disclosure is realized as follows: an ultrasonic-microwave synergistic extraction method of total saponins in beautiful *millettia* root comprises the following steps:

S1, material treatment: washing and air-drying beautiful *millettia* root, and sending the air-dried beautiful *millettia* root into a dryer to be continuously and dynamically dried with hot air at 40-60° C. until the moisture content of the beautiful *millettia* root is less than 10% to obtain dried beautiful *millettia* root;

S2, cold soaking: cutting the dried beautiful *millettia* root into a section, putting the beautiful *millettia* root section into a dichloromethane solvent with a volume fraction of 70-90% for cold soaking, performing stirring for 2-4 h after the first cold soaking for 1-3 days, performing stirring for 1-2 h after the second cold soaking for 2-4 days, and performing filtration to obtain a cold soaking section of beautiful *millettia* root; S3, enzymatic hydrolysis: mixing a yeast protease with distilled water to prepare a yeast protease solution, soaking the cold soaking section of beautiful *millettia* root in the yeast protease solution, and performing pressurized hydrolysis at a temperature of 30-50° C., a relative humidity of 60-100%, and a pressure of 1.2-2.0 MPa for 2-4 h;

S4, extract extraction: adding an ether solvent into the enzymatically hydrolyzed beautiful *millettia* root, performing stirring and reflux extraction at 38-45° C. for 30-50 min, performing filtration, collecting a residue for standby use, and concentrating a filtrate under reduced pressure to obtain a beautiful *millettia* root extract, wherein the addition of the ether solvent into the enzymatically hydrolyzed beautiful *millettia* root helps to remove fat-soluble impurities; and S5, ultrasonic-microwave synergistic extraction: mixing the beautiful *millettia* root extract in S4 and water-saturated n-butanol at a mass-volume ratio g/mL of 1:(3-5), putting the mixture into an ultrasonic-microwave synergistic extraction tank for extraction, collecting an upper phase, and performing concentration and precipitation to obtain total saponins in beautiful *millettia* root.

Furthermore, a mass-volume ratio g/mL of the beautiful *millettia* root dried in S2 to the dichloromethane solvent is (0.3-0.8):(1-5).

Furthermore, the yeast protease solution in S3 is prepared by mixing the yeast protease and the distilled water at a volume ratio of 1:(5-12).

Furthermore, a mass-volume ratio g/mL of the beautiful *millettia* root enzymatically hydrolyzed in S4 and the ether solvent is 1:(3-8).

Furthermore, in the ultrasonic-microwave synergistic extraction of S5, a microwave frequency is 1,500-2,000 MHz and a power is 2-8 KW.

Furthermore, in the ultrasonic-microwave synergistic extraction of S5, an ultrasonic wave frequency is 30-60 KHz and a power is 0.8-2 KW.

Furthermore, the ultrasonic-microwave synergistic extraction of S5 is performed at a temperature of 40-50° C. for 20-60 min.

Compared with the traditional art, the present disclosure has the beneficial effects that:

The ultrasonic-microwave synergistic extraction method of total saponins in beautiful *millettia* root extracts relatively high content of total saponins, and has relatively high yield of saponins and low content of impurities. The beautiful *millettia* root is dried and subjected to cold soaking, and thus epidermal cells of the beautiful *millettia* root are broken, an adsorption force between chemical components in the beautiful *millettia* root and histiocytes is overcome, and effective components in the beautiful *millettia* root are extracted while floccule such as pectin and the like are removed. An enzyme protease solution is added for enzymatic hydrolysis, saponin is hydrolyzed to obtain sapogenin, which facilitates the subsequent extraction. A reflux extraction using an ether solvent helps to remove fat-soluble impurities. An ultrasonic-microwave synergistic extraction is used, frequency and power are controlled, and synergistic extraction is performed, such that bubbling of the saponin in the extraction process can be inhibited and the purity of the saponin is improved.

DESCRIPTION OF THE EMBODIMENTS

In order to better understand the technical content of the present disclosure, specific examples will be provided below to further illustrate the present disclosure.

Unless otherwise specified, all experimental methods used in the examples of the present disclosure are conventional methods.

All materials and reagents used in the examples of the present disclosure may be commercially available, unless otherwise specified.

Example 1

An ultrasonic-microwave synergistic extraction method of total saponins in beautiful *millettia* root comprised the following steps:

S1, material treatment: beautiful *millettia* root was washed and air-dried, and the air-dried beautiful *millettia* root was sent into a dryer to be continuously and dynamically dried with hot air at 40° C. until the moisture content of the beautiful *millettia* root was less than 10% to obtain dried beautiful *millettia* root;

S2, cold soaking: the dried beautiful *millettia* root was cut into a section, the beautiful *millettia* root section was put into a dichloromethane solvent with a volume fraction of 70% for cold soaking, wherein a mass-volume ratio g/mL of the dried beautiful *millettia* root to the dichloromethane solvent was 0.3:1, stirring was performed for 2 h after the first cold soaking for 1 day, stirring was performed for 1 h after the second cold soaking for 2 days, and filtration was performed to obtain a cold soaking section of beautiful *millettia* root;

S3, enzymatic hydrolysis: a yeast protease was mixed with distilled water at a volume ratio of 1:(5-12) to prepare a yeast protease solution, the cold soaking section of beautiful *millettia* root was soaked in the yeast protease solution, and pressurized hydrolysis was performed at a temperature of 30° C., a relative humidity of 60%, and a pressure of 1.2 MPa for 2 h;

S4, extract extraction: an ether solvent was added into the enzymatically hydrolyzed beautiful *millettia* root at a mass-volume ratio g/mL of 1:3, stirring and reflux extraction were performed at 38° C. for 30 min, filtration was performed, a residue was collected for standby use, and a filtrate was concentrated under reduced pressure to obtain a beautiful *millettia* root extract; and S5, ultrasonic-microwave synergistic extraction: the beautiful *millettia* root extract in S4 and water-saturated n-butanol were mixed at a mass-volume ratio g/mL of 1:3, the mixture was put into an ultrasonic-microwave synergistic extraction tank for extraction at a microwave frequency of 1,500 MHz and a power of 2 KW, an ultrasonic wave frequency of 30 KHz and a power of 0.8 KW, and a temperature of 40° C. for 20 min, an upper phase was collected, and concentration and precipitation were performed to obtain total saponins in beautiful *millettia* root.

Example 2

An ultrasonic-microwave synergistic extraction method of total saponins in beautiful *millettia* root comprised the following steps:

S1, material treatment: beautiful *millettia* root was washed and air-dried, and the air-dried beautiful *millettia* root was sent into a dryer to be continuously and dynamically dried with hot air at 60° C. until the moisture content of the beautiful *millettia* root was less than 10% to obtain dried beautiful *millettia* root;

S2, cold soaking: the dried beautiful *millettia* root was cut into a section, the beautiful *millettia* root section was put into a dichloromethane solvent with a volume fraction of 90% for cold soaking, wherein a mass-volume ratio g/mL of the dried beautiful *millettia* root to the dichloromethane solvent was 0.8:5, stirring was performed for 4 h after the first cold soaking for 3 days, stirring was performed for 2 h after the second cold soaking for 4 days, and filtration was performed to obtain a cold soaking section of beautiful *millettia* root;

S3, enzymatic hydrolysis: a yeast protease was mixed with distilled water at a volume ratio of 1:12 to prepare a yeast protease solution, the cold soaking section of beautiful *millettia* root was soaked in the yeast protease solution, and pressurized hydrolysis was performed at a temperature of 30-50° C., a relative humidity of 100%, and a pressure of 2 MPa for 4 h;

S4, extract extraction: an ether solvent was added into the enzymatically hydrolyzed beautiful *millettia* root at a mass-volume ratio g/mL of 1:8, stirring and reflux extraction were performed at 45° C. for 50 min, filtration was performed, a residue was collected for standby use, and a filtrate was concentrated under reduced pressure to obtain a beautiful *millettia* root extract; and S5, ultrasonic-microwave synergistic extraction: the beautiful *millettia* root extract in S4 and water-saturated n-butanol were mixed at a mass-volume ratio g/mL of 1:5, the mixture was put into an ultrasonic-microwave synergistic extraction tank for extraction at a microwave frequency of 2,000 MHz and a power of 8 KW, an ultrasonic wave frequency of 60 KHz and a power of 2 KW, and a temperature of 50° C. for 60 min, an upper phase was collected, and concentration and precipitation were performed to obtain total saponins in beautiful *millettia* root.

Example 3

An ultrasonic-microwave synergistic extraction method of total saponins in beautiful *millettia* root comprised the following steps:

S1, material treatment: beautiful *millettia* root was washed and air-dried, and the air-dried beautiful *millettia* root was sent into a dryer to be continuously and dynamically dried with hot air at 50° C. until the moisture content of the beautiful *millettia* root was less than 10% to obtain dried beautiful *millettia* root;

S2, cold soaking: the dried beautiful *millettia* root was cut into a section, the beautiful *millettia* root section was put into a dichloromethane solvent with a volume fraction of 80% for cold soaking, wherein a mass-volume ratio g/mL of the dried beautiful *millettia* root to the dichloromethane solvent was 0.5:3, stirring was performed for 3 h after the first cold soaking for 2 days, stirring was performed for 1.5 h after the second cold soaking for 3 days, and filtration was performed to obtain a cold soaking section of beautiful *millettia* root;

S3, enzymatic hydrolysis: a yeast protease was mixed with distilled water at a volume ratio of 1:8 to prepare a yeast protease solution, the cold soaking section of beautiful *millettia* root was soaked in the yeast protease solution, and pressurized hydrolysis was performed at a temperature of 30-50° C., a relative humidity of 80%, and a pressure of 1.5 MPa for 3 h;

S4, extract extraction: an ether solvent was added into the enzymatically hydrolyzed beautiful *millettia* root at a mass-volume ratio g/mL of 1:5, stirring and reflux extraction were performed at 40° C. for 40 min, filtration was performed, a residue was collected for standby use, and a filtrate was concentrated under reduced pressure to obtain a beautiful *millettia* root extract; and S5, ultrasonic-microwave synergistic extraction: the beautiful *millettia* root extract in S4 and water-saturated n-butanol were mixed at a mass-volume ratio g/mL of 1:4, the mixture was put into an ultrasonic-microwave synergistic extraction tank for extraction at a microwave frequency of 1,800 MHz and a power of 6 KW, an ultrasonic wave frequency of 50 KHz and a power of 1.5 KW, and a temperature of 45° C. for 24 min, an upper phase was collected, and concentration and precipitation were performed to obtain total saponins in beautiful *millettia* root.

Example 4

The difference between the example and example 3 was that a mass-volume ratio g/mL of the beautiful *millettia* root dried in S2 to the dichloromethane solvent was 0.2:8.

Example 5

The difference between the example and example 3 was that a mass-volume ratio g/mL of the beautiful *millettia* root enzymatically hydrolyzed in S4 and the ether solvent is 1:10.

Example 6

The difference between the example and example 3 was that in the ultrasonic-microwave synergistic extraction of S5, a microwave frequency was 1,000 MHz and a power was 10 KW.

Comparative Example 1

The difference between the comparative example and example 3 was that the dried beautiful *millettia* root was not subjected to cold soaking by the dichloromethane solvent; and specifically, the ultrasonic-microwave synergistic extraction method of total saponins in beautiful *millettia* root comprised the following steps:

S1, material treatment: beautiful *millettia* root was washed and air-dried, and the air-dried beautiful *millettia* root was sent into a dryer to be continuously and dynamically dried with hot air at 50° C. until the moisture content of the beautiful *millettia* root was less than 10% to obtain dried beautiful *millettia* root;

S2, enzymatic hydrolysis: a yeast protease was mixed with distilled water at a volume ratio of 1:8 to prepare a yeast protease solution, the dried beautiful *millettia* root was soaked in the yeast protease solution, and pressurized hydrolysis was performed at a temperature of 30-50° C., a relative humidity of 80%, and a pressure of 1.5 MPa for 3 h;

S3, extract extraction: an ether solvent was added into the enzymatically hydrolyzed beautiful *millettia* root at a mass-volume ratio g/mL of 1:5, stirring and reflux extraction were performed at 40° C. for 40 min, filtration was performed, a residue was collected for standby use, and a filtrate was concentrated under reduced pressure to obtain a beautiful *millettia* root extract; and S4, ultrasonic-microwave synergistic extraction: the beautiful *millettia* root extract in S4 and water-saturated n-butanol were mixed at a mass-volume ratio g/mL of 1:4, the mixture was put into an ultrasonic-microwave synergistic extraction tank for extraction at a microwave frequency of 1,800 MHz and a power of 6 KW, an ultrasonic wave frequency of 50 KHz and a power of 1.5 KW, and a temperature of 45° C. for 24 min, an upper phase was collected, and concentration and precipitation were performed to obtain total saponins in beautiful *millettia* root.

Comparative Example 2

The difference between the comparative example and example 3 was that the cold soaking section of beautiful *millettia* root was not subjected to enzymatic hydrolysis; and specifically, the ultrasonic-microwave synergistic extraction method of total saponins in beautiful *millettia* root comprised the following steps:

S1, material treatment: beautiful *millettia* root was washed and air-dried, and the air-dried beautiful *millettia* root was sent into a dryer to be continuously and dynamically dried with hot air at 50° C. until the moisture content of the beautiful *millettia* root was less than 10% to obtain dried beautiful *millettia* root;

S2, cold soaking: the dried beautiful *millettia* root was cut into a section, the beautiful *millettia* root section was put into a dichloromethane solvent with a volume fraction of 80% for cold soaking, wherein a mass-volume ratio g/mL of the dried beautiful *millettia* root to the dichloromethane solvent was 0.5:3, stirring was performed for 3 h after the first cold soaking for 2 days, stirring was performed for 1.5 h after the second cold soaking for 3 days, and filtration was performed to obtain a cold soaking section of beautiful *millettia* root;

S3, extract extraction: an ether solvent was added into the cold soaking section of beautiful *millettia* root at a mass-volume ratio g/mL of 1:5, stirring and reflux extraction were performed at 40° C. for 40 min, filtration was performed, a residue was collected for standby use, and a filtrate was concentrated under reduced pressure to obtain a beautiful *millettia* root extract; and S4, ultrasonic-microwave synergistic extraction: the beautiful *millettia* root extract in S4 and water-saturated n-butanol were mixed at a mass-volume ratio g/mL of 1:4, the mixture was put into an ultrasonic-microwave synergistic extraction tank for extraction at a microwave frequency of 1,800 MHz and a power of 6 KW, an ultrasonic wave frequency of 50 KHz and a power of 1.5 KW, and a temperature of 45° C. for 24 min, an upper phase was collected, and concentration and precipitation were performed to obtain total saponins in beautiful *millettia* root.

Comparative Example 3

The difference between the comparative example and example 3 was that the extraction was ultrasonic-assisted extraction; and specifically, the ultrasonic-assisted extraction method of total saponins in beautiful *millettia* root comprised the following steps:

S1, material treatment: beautiful *millettia* root was washed and air-dried, and the air-dried beautiful *millettia* root was sent into a dryer to be continuously and dynamically dried with hot air at 50° C. until the moisture content of the beautiful *millettia* root was less than 10% to obtain dried beautiful *millettia* root;

S2, cold soaking: the dried beautiful *millettia* root was cut into a section, the beautiful *millettia* root section was put into a dichloromethane solvent with a volume fraction of 80% for cold soaking, wherein a mass-volume ratio g/mL of the dried beautiful *millettia* root to the dichloromethane solvent was 0.5:3, stirring was performed for 3 h after the first cold soaking for 2 days, stirring was performed for 1.5 h after the second cold soaking for 3 days, and filtration was performed to obtain a cold soaking section of beautiful *millettia* root;

S3, enzymatic hydrolysis: a yeast protease was mixed with distilled water at a volume ratio of 1:8 to prepare a yeast protease solution, the cold soaking section of beautiful *millettia* root was soaked in the yeast protease solution, and pressurized hydrolysis was performed at a temperature of 30-50° C., a relative humidity of 80%, and a pressure of 1.5 MPa for 3 h;

S4, extract extraction: an ether solvent was added into the enzymatically hydrolyzed beautiful *millettia* root at a mass-volume ratio g/mL of 1:5, stirring and reflux extraction were performed at 40° C. for 40 min, filtration was performed, a residue was collected for standby use, and a filtrate was concentrated under reduced pressure to obtain a beautiful *millettia* root extract; and S5, ultrasonic-assisted extraction: the beautiful *millettia* root extract in S4 and water-saturated n-butanol were mixed at a mass-volume ratio g/mL of 1:4, the mixture was put into an ultrasonic extraction tank for extraction at an ultrasonic wave frequency of 50 KHz and a power of 1.5 KW, and a temperature of 45° C. for 24 min, an upper phase was collected, and concentration and precipitation were performed to obtain total saponins in beautiful *millettia* root.

Comparative Example 4

The difference between the comparative example and example 3 was that the extraction was microwave-assisted extraction; and specifically, the microwave-assisted extraction method of total saponins in beautiful *millettia* root comprised the following steps:

S1, material treatment: beautiful *millettia* root was washed and air-dried, and the air-dried beautiful *millettia* root was sent into a dryer to be continuously and dynamically dried with hot air at 50° C. until the moisture content of the beautiful *millettia* root was less than 10% to obtain dried beautiful *millettia* root;

S2, cold soaking: the dried beautiful *millettia* root was cut into a section, the beautiful *millettia* root section was put into a dichloromethane solvent with a volume fraction of 80% for cold soaking, wherein a mass-volume ratio g/mL of the dried beautiful *millettia* root to the dichloromethane solvent was 0.5:3, stirring was performed for 3 h after the first cold soaking for 2 days, stirring was performed for 1.5 h after the second cold soaking for 3 days, and filtration was performed to obtain a cold soaking section of beautiful *millettia* root;

S3, enzymatic hydrolysis: a yeast protease was mixed with distilled water at a volume ratio of 1:8 to prepare a yeast protease solution, the cold soaking section of beautiful *millettia* root was soaked in the yeast protease solution, and pressurized hydrolysis was performed at a temperature of 30-50° C., a relative humidity of 80%, and a pressure of 1.5 MPa for 3 h;

S4, extract extraction: an ether solvent was added into the enzymatically hydrolyzed beautiful *millettia* root at a mass-volume ratio g/mL of 1:5, stirring and reflux extraction were performed at 40° C. for 40 min, filtration was performed, a residue was collected for standby use, and a filtrate was concentrated under reduced pressure to obtain a beautiful *millettia* root extract; and S5, microwave-assisted extraction: the beautiful *millettia* root extract in S4 and water-saturated n-butanol were mixed at a mass-volume ratio g/mL of 1:4, the mixture was put into a microwave extraction tank for extraction at a microwave frequency of 1,800 MHz and a power of 6 KW, and a temperature of 45° C. for 24 min, an upper phase was collected, and concentration and precipitation were performed to obtain total saponins in beautiful *millettia* root.

1. Result Determination

The total saponins extracted from beautiful *millettia* root in examples 1-6 and comparative examples 1~4 were analyzed by high performance liquid chromatography (HPLC), and the conditions were as follows:

(1) chromatographic column: Sephadex LH;

(2) mobile phase A: water; and mobile phase B: acetonitrile;

(3) flowing rate: 1 mL/min;

(4) detection wavelength: 545 nm; and (5) injection volume: 20 mL.

Total volume, integral peak area, and weight were analyzed according to an HPLC chromatogram, and the total saponin content and the total saponin yield were calculated.

Total saponin yield=m/M×100%, m is the mass of total saponins extracted from beautiful *millettia* root in the present disclosure and M is the total saponin mass of beautiful *millettia* root.

The results were as follows:

|  | Total saponin content (%) | Total saponin yield (%) |
| --- | --- | --- |
| Example 1 | 97.1 | 98.0 |
| Example 2 | 97.3 | 98.2 |
| Example 3 | 98.8 | 98.3 |
| Example 4 | 92.6 | 96.5 |
| Example 5 | 93.9 | 95.8 |
| Example 6 | 91.2 | 96.0 |
| Comparative example 1 | 87.5 | 90.1 |
| Comparative example 2 | 86.1 | 89.2 |
| Comparative example 3 | 87.2 | 88.3 |
| Comparative example 4 | 82.9 | 87.9 |

The results showed that the extraction method of the present disclosure removed fat-soluble impurities and water-soluble impurities, efficiently separated substances such as saponin and structural analogues thereof, realized high-purity preparation of total saponins, and improved the total saponin yield. When examples 1-6 were compared with comparative example 1, it can be known that after the beautiful *millettia* root was subjected to the cold soaking by using the dichloromethane solvent, an adsorption force between chemical components in the beautiful *millettia* root and histiocytes was overcome, and the effective components in the beautiful *millettia* root can be extracted. When comparative example 2 was compared, the cold soaking section of beautiful *millettia* root was enzymatically hydrolyzed to hydrolyze the saponin into sapogenin. When comparative examples 3 and 4 were compared, the ultrasonic-microwave synergistic extraction was used, frequency and power were controlled, under the same extraction temperature, a better assisted extraction effect can be reached, bubbling of the saponin in the extraction process was inhibited, impurities were reduced, and the purity of the saponin was improved.

The above descriptions are only preferred examples of the present disclosure and are not intended to limit the present disclosure. Any modification, equivalent substitution, and improvement made within the spirit and principle of the present disclosure shall be included in the protection scope of the present disclosure.

What is claimed is:

1. An ultrasonic-microwave synergistic extraction method of total saponins in beautiful *millettia* root, comprising the following steps:

S1, material treatment: washing and air-drying beautiful *millettia* root, and sending the air-dried beautiful *millettia* root into a dryer to be continuously and dynamically dried with hot air at 40-60° C. until the moisture content of the beautiful *millettia* root is less than 10% to obtain dried beautiful *millettia* root;

S2, cold soaking: cutting the dried beautiful *millettia* root into a section, putting the beautiful *millettia* root section into a dichloromethane solvent with a volume fraction of 70-90% for cold soaking, wherein a mass-volume ratio g/mL of the beautiful *millettia* root to the dichloromethane solvent is (0.3-0.8):(1-5), performing stirring for 2-4 h after the first cold soaking for 1-3 days, performing stirring for 1-2 h after the second cold soaking for 2-4 days, and performing filtration to obtain a cold soaking section of beautiful *millettia* root;

S3, enzymatic hydrolysis: mixing a yeast protease with distilled water to prepare a yeast protease solution, soaking the cold soaking section of beautiful *millettia* root in the yeast protease solution, and performing pressurized hydrolysis at a temperature of 30-50° C., a relative humidity of 60-100%, and a pressure of 1.2-2.0 MPa for 2-4 h, wherein the yeast protease solution is prepared by mixing the yeast protease and the distilled water at a volume ratio of 1:(5-12);

S4, extract extraction: adding an ether solvent into the enzymatically hydrolyzed beautiful *millettia* root, wherein a mass-volume ratio g/mL of the beautiful *millettia* root and the ether solvent is 1:(3-8), performing stirring and reflux extraction at 38-45° C. for 30-50 min, performing filtration, collecting a residue for standby use, and concentrating a filtrate under reduced pressure to obtain a beautiful *millettia* root extract; and S5, ultrasonic-microwave synergistic extraction: mixing the beautiful *millettia* root extract in S4 and water-saturated n-butanol at a mass-volume ratio g/mL of 1:(3-5), putting the mixture into an ultrasonic-microwave synergistic extraction tank for extraction at a microwave frequency of 1,500-2,000 MHz and a power of 2-8 KW, an ultrasonic wave frequency of 30-60 KHz and a power of 0.8-2 KW, and a temperature of 40-50° C. for 20-60 min, collecting an upper phase, and performing concentration and precipitation to obtain total saponins in beautiful *millettia* root.

* * * * *